(12) United States Patent
Foggi et al.

(10) Patent No.: US 10,704,996 B2
(45) Date of Patent: Jul. 7, 2020

(54) MACHINERY FOR AN AUTOMATED ANALYSIS OF THE SLIDES IN ACCORDANCE WITH THE INDIRECT IMMUNOFLUORESCENCE ASSAY—IFA

(71) Applicant: A.M.T. S.R.L., San Giovanni Valdarno (IT)

(72) Inventors: Alessandro Foggi, San Giovanni Valdarno (IT); Gabriele Donati, Pescia (IT)

(*) Notice: Subject to any disclaimer, the term of this patent is extended or adjusted under 35 U.S.C. 154(b) by 193 days.

(21) Appl. No.: 15/574,459

(22) PCT Filed: Jun. 9, 2016

(86) PCT No.: PCT/IB2016/053405
§ 371 (c)(1),
(2) Date: Nov. 15, 2017

(87) PCT Pub. No.: WO2016/199064
PCT Pub. Date: Dec. 15, 2016

(65) Prior Publication Data
US 2018/0136096 A1 May 17, 2018

(30) Foreign Application Priority Data
Jun. 12, 2015 (IT) .......................... 102015000023146

(51) Int. Cl.
*G01N 1/31* (2006.01)
*G01N 1/18* (2006.01)
(Continued)

(52) U.S. Cl.
CPC ............... *G01N 1/312* (2013.01); *G01N 1/18* (2013.01); *G01N 33/483* (2013.01); *G01N 33/53* (2013.01); *G01N 35/00029* (2013.01)

(58) Field of Classification Search
CPC ............ G01N 1/312; G01N 35/00029; G01N 33/483; G01N 1/18; G01N 33/53;
(Continued)

(56) References Cited

U.S. PATENT DOCUMENTS 6,495,106 B1 12/2002 Kalra
2005/0250211 A1* 11/2005 Reinhardt ................. B01L 9/52
436/43
(Continued)

FOREIGN PATENT DOCUMENTS

EP 2587296 5/2013
WO 2014132094 9/2014

*Primary Examiner* — Benjamin R Whatley
*Assistant Examiner* — Curtis A Thompson
(74) *Attorney, Agent, or Firm* — Themis Law

(57) ABSTRACT

A machinery for preparation and analysis of one or more slides for a biological material according to an immunofluorescence technique includes a loading station for one or more containers of test liquids and/or samples of product; a positioning station of the slides; a containment station of one or more slide covers; an analysis station having a microscope that acquires digital images at one or more magnifications; an assembly, mobile inside the area defined by the machinery and controlled to move through the stations to prepare one or more slides according to a predefined protocol and arrange them in a corresponding analysis station for subsequent acquisition of digital images; one or more covers for each slide arranged in the seat; a container of the covers, the assembly being controlled to remove the covers once the phase of pre-dilution of the samples has been completed and arrange them inside the container.

12 Claims, 13 Drawing Sheets

(51) Int. Cl.
*G01N 33/483* (2006.01)
*G01N 35/00* (2006.01)
*G01N 33/53* (2006.01)

(58) Field of Classification Search
CPC ........... G01N 2021/7786; G01N 21/64; G01N 2030/8804; G01N 21/6486; G06T 2207/10064; G04D 1/0071; G04D 1/0078
See application file for complete search history.

(56) References Cited

U.S. PATENT DOCUMENTS

| | | | |
|---|---|---|---|
| 2006/0120921 A1* | 6/2006 | Elliot | B01L 3/545 422/63 |
| 2012/0003627 A1 | 1/2012 | Scholl | |
| 2012/0108461 A1* | 5/2012 | Bussan | G01N 35/00029 506/9 |
| 2013/0034874 A1* | 2/2013 | Peltier | G01N 35/10 435/29 |
| 2014/0273086 A1 | 9/2014 | Lefebvre | |
| 2016/0011221 A1* | 1/2016 | Hegedus | G01N 35/00029 435/286.3 |

* cited by examiner

MACHINERY FOR AN AUTOMATED ANALYSIS OF THE SLIDES IN ACCORDANCE WITH THE INDIRECT IMMUNOFLUORESCENCE ASSAY—IFA

TECHNICAL FIELD

The present invention refers to the technical field of equipment for the analysis of the slides on which biological material of a patient is placed in order to check the presence of pathologies in general (in accordance with the IFA technique—Indirect immunofluorescence assay=Indirect Fluorescent Antibody Test).

In particular, the invention refers to a particularly versatile machinery that allows to execute diagnostic analysis of auto-immune pathologies passing through a completely automatic process of preparation and reading of slides, from the biological sample directly to the analysis at the computer and rendering eventually the digitalized images available via the Internet.

BACKGROUND ART

The indirect immunofluorescence assay (IFA) is one of the most used techniques in immunology to detect in a certain sample the presence of specific unknown antigens or antibodies whose known counterpart is variously linked to a fluorophore. The fluorophore is a fluorochrome, generally fluorescein, which absorbing ultraviolet rays emits a green light and therefore an observable light with an illuminated microscope.

The method of analysis foresees that in the research of the unknown antibody the sample, appropriately diluted with a phosphate buffer or a saline solution, is put in contact with known antigens and fixed on the window of a slide. The slide is thus characterized by an assembly of windows (dedicated areas) on which the analysis are done.

The substrate is therefore treated and prepared with appropriate known methods, in such a way as to generate a specific antigen. It is useful to remember here that the antigen is any element extraneous to the organism, capable of inducing an immunospecific response with the generation of a population of reactive lymphocytes B and consequent production of specific antibodies.

If a specific illness is researched, a specific substrate is arranged that represents a specific antigen capable of linking with the specific antibodies eventually present in the sample under exam, in case it is infected.

The operation of arrangement of the sample on the window must be done in a few minutes, otherwise a process of degeneration of the substrate starts and all the results risk to be distorted.

After arranging the sample on the window, and waiting for the necessary incubation time, an accurate wash with a buffer solution must be done and an anti-immunoglobulin antiserum must be added, of the species from which the serum under exam comes from, marked with fluorescein (FITC).

After waiting a further incubation time, the antiserum is washed again with a buffer solution.

At the end of this phase, on each window there is applied mounting medium to preserve the fluorescence from a quick decay. It is finally arranged on the slide a cover slide that has a thickness generally of about a tenth of a millimeter. The mounting medium is a solution of glycerol at 10% in PBS that is used to "crystallize" the situation obtained on the window and guarantee a better retention of the fluorescent light. At this point, the cover slide is applied that has a thickness generally of about a tenth of a millimeter, for example 0.2 mm. At the current state, it is applied by hand and moved with a suction pen. The cover slide intensifies the duration of the complex biochemicals obtained but must be applied with care to avoid the formation of bubbles that would affect the subsequent vision at the microscope.

At this point, the slide is ready for the analysis at the microscope through the use of objectives of 20.times. and 40.times. magnification and the presence of the antibody conjugated with the fluorophore thus becomes an evidence of the presence of the illness researched.

At the current state of the art, the necessary procedures described above are done totally or in part manually, the whole requiring the continuous presence of an operator and above all lengthening the procedure times. In particular, the operations of preparation of the slide can be manual and its subsequent transfer in the section of the microscope is manual. Not only does the whole lengthen the analysis times but it also risks to make exceed said limit times within which the slide must be arranged, avoiding deteriorations of the materials in analysis that would render the subsequent detections vane.

Currently, there exist automatic preparers (processors) that at the end of their preparation process provide slides that, following an operation of manual assembly (deposition on the slide of a fixing liquid and positioning of the cover slide), are ready for the reading and interpretation at the traditional microscope. A feature of these slides is the rapid decay of the fluorescent signal that is read at the microscope and therefore require a quick reading after their preparation and are not re-usable after a long time for a subsequent re-reading.

As for the reading at the microscope in the past, instead, a telecamera was mounted on the microscope and some fields of interest were photographed and saved in the computer. The choice of the fields was at the operator's discretion. In the last years automatic acquisition and interpretation systems have been introduced, which operate as follows: acquisition of a pre-set number of images per window in pre-defined positions with subsequent automatic discrimination of the positive/negative cases and recognition of the cellular pattern. In the cases in which the operator is not sure of the automatic evaluation done by the software, it is indispensable to re-evaluate the slide at the traditional microscope because the number of fields acquired is not sufficient to visualize the entire slide and complete the evaluation in each situation.

To date, ultimately and considering what has been said so far, the process of diagnostic analysis of biological samples in autoimmunity takes place according to the following steps:

The operator inserts the samples in the system of preparation of the slides;

The system prepares the slides automatically;

The operator takes off the slides and assembles them manually (adding "Mounting Medium" and cover slide);

The operator reads at the traditional microscope the slide or acquires some fields of the slide in the case in which an automatic reading system at the microscope is present.

It results evident that during the process the continuous presence of an operator is required and that after some days the slides are deteriorated and not readable anymore due to the loss of the fluorescent signal.

Publication WO2014/132094 is further known, which corresponds to the preamble of claim 1.

Such publication describes a machinery that allows to automatize a good part of the process of analysis of a slide.

The machinery foresees a loading station of the slides and a mobile system that prepares the slides with the various necessary reagents. The slide is then automatically moved under a unit of acquisition of the images where all the images at various magnifications are acquired, to be able to be then normally analyzed also from remote.

The machinery described in such publication, even if being able to automatize the process, is not exempt from some technical inconveniences, in particular in the field of auto-immunity.

The process of preparation of the slide and analysis is not in fact totally automatized, requiring the presence of an operator at least during all the preparatory phase of the slide.

In particular, it is known that is it necessary a pre-dilution phase of the samples that can require a variable time, sometimes also some hours, for its completion. In that sense, the operation of loading of the slides in the machine must take place, through an operator, only after the operator has done the dilution of samples and such operation has been completed.

In that sense, in accordance with said publication and with the known machines in general that operate in the field of auto-immunity, at the current state it is impossible to arrange contextually the slides in the machine and start a pre-dilution phase of the samples, since the time within which the deterioration of the substrate initiates due to the moisture of the air can be of about 15-30 minutes, while the operation of pre-dilution can require longer times, also a couple of hours.

In a preliminary phase, therefore, the presence of an operator is necessary that first starts the pre-dilution of the liquids, waits for the completion of such operation and then loads the slides on the machinery. All this, actually, evidently renders the machine automatic only in part.

DISCLOSURE OF INVENTION

It is therefore the aim of the present invention to provide a machinery that solves said technical inconveniences.

In particular, it is the aim of the present invention to provide a totally automatic machine, in which the processing times are optimized, in which the constant presence of an operator is not required and in which the total automatization allows a quick and precise working.

These and other aims are obtained with the present machinery for the preparation and the analysis of one or more slides according to an immunofluorescence technique as described hereinafter.

Such machinery comprises:

A loading station suitable for the arrangement of one or more containers for the containment of test liquids and/or samples of product. Such station is preferably removable from the machinery to facilitate the preparation of the products to be then re-positioned.

A positioning station of one or more slides. Also this one is preferably removable to facilitate the arrangement of the slides to be then re-positioned. Such positioning station comprises a support base provided with a plurality of seats suitable for holding the slide;

A containment station of one or more cover slides;

An analysis station comprising a microscope, preferably digital, for the digital acquisition of the images at one or more magnifications;

It is further foreseen a loading system mobile inside the area defined by the machinery and controlled in such a way as to move through said stations so as to prepare one or more slides in accordance with a pre-defined protocol (previously programmed) and arrange said slide/s in the corresponding analysis station for a subsequent acquisition of one or more digital images.

In accordance with the invention, the following are further foreseen:

One or more covers of such a size as to be applied to cover each slide arranged in the seat;

A container for the containment of one or more of said covers;

And wherein the loading system is further controlled to operate the removal of the cover/s, once the phase of pre-dilution of the samples has been completed, and arrange it/them inside the container.

In this manner, all said technical inconveniences are solved.

In particular, the machinery now results totally automatic and capable of integrating an under-system for the preparation of the slides with an under-system for the complete scanning, digitalization and analysis of the slides.

The constant presence of an operator is not necessary anymore and there is no risk of decay of the samples to analyze because they result now in images of the digitalized windows.

In order to reach such aim, the system guarantees:

The semi-automatic insertion of the biological samples in the machinery in the loading station;

The automatic preparation of the slides and the relative automatic assembly of the slides thanks to the loading system.

The complete scanning and automatic interpretation of the slides thanks to the station provided with microscope;

The automatic saving of the digital slides in the PC with subsequent reading also from remote via the Intranet/Internet, through the use of the virtual microscope.

The use of the covers, which are manually arranged on the slides loaded in their respective seats, allows a subsequent total automation of the process. From that moment, in fact, the machine initiates to prepare the various liquids that are then adequately arranged on the slides, in accordance with the foreseen protocol. The cover avoids the degeneration of the material on the slide and therefore the slides can be loaded before starting the phase of pre-dilution of the samples, making the process result totally automatized and avoiding that the operator has to first wait for the completion of the pre-dilution to then go back to loading the slides in the respective seats and start the machine for its processing work.

It is thus realized a totally walkaway process and the digital conservation of the slide is guaranteed, overcoming the problem of deterioration in time.

Once the test is concluded the machinery is therefore capable of indicating a response of positivity for each test done, identifying also the cellular pattern.

In particular, the complete digitalization of the slide and the use of a virtual microscope presents the following advantages:

Vision of the digital slide on the system or from remote without loss of information and without the need to review it at the traditional microscope;

Vision of the slide repeatedly in time without loss of the signal. In fact, the digital slide remains unaltered in time, while the fluorescence signal decays in time;

Vision at low digital magnification with high emission of fluorescence: in fact the case visualized at low magnification is obtained from images acquired at high magnification and therefore presents a high emission of fluorescence. In the traditional microscope the vision at low magnification takes place at low emission of fluorescence because the excitation energy transmitted through the objective is very low.

Further features can be deduced from the dependent claims.

BRIEF DESCRIPTION OF DRAWINGS

Further features and advantages of the present machinery, according to the invention, will result clearer with the description that follows of some embodiments, made to illustrate but not to limit, with reference to the annexed drawings, wherein.

DESCRIPTION OF SOME PREFERRED EMBODIMENTS

In accordance with the present description a structural description of the invention and subsequently a description of functioning and use of the machinery are furnished.

Figure 1:
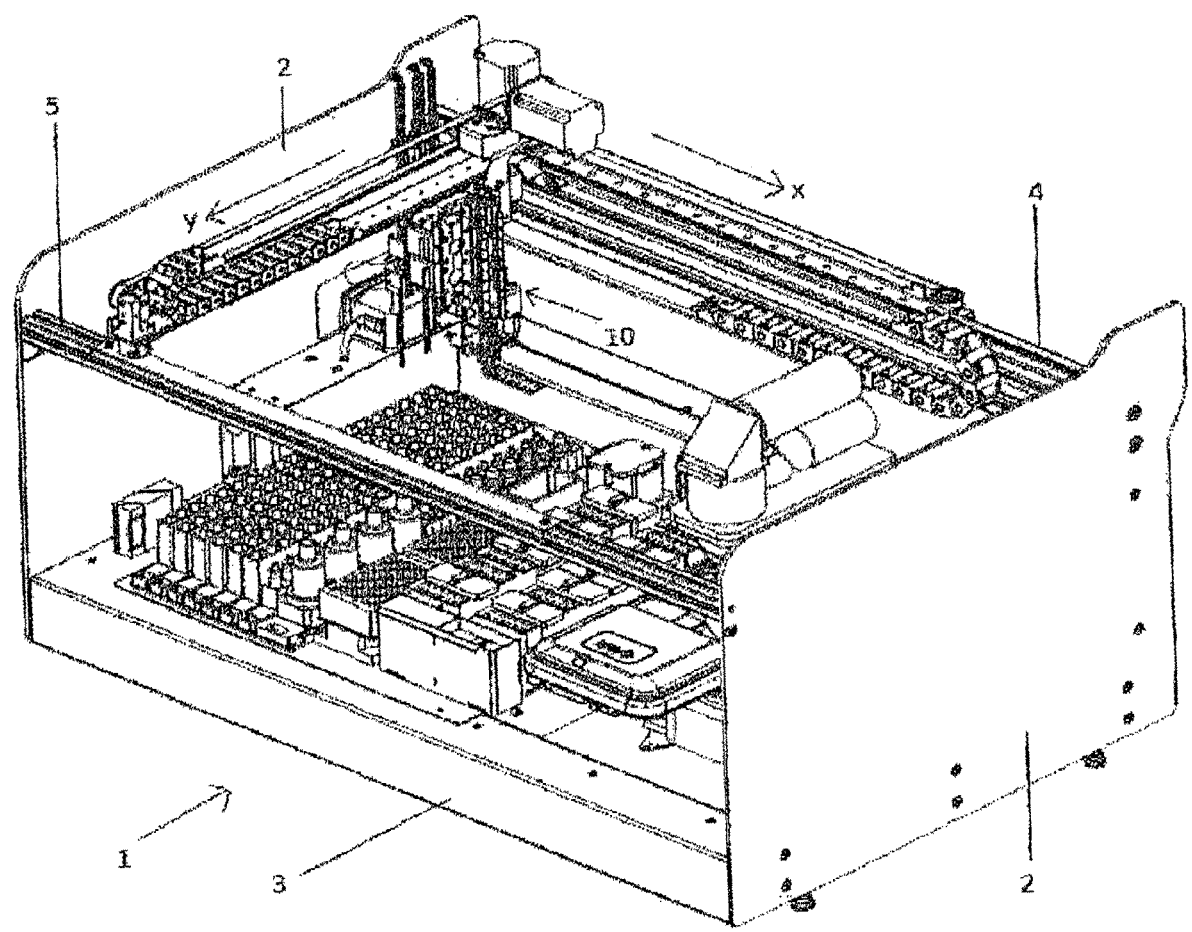
FIG. 1 shows an axonometric view of the present invention.

From the structural point of view, FIG. 1 describes in an axonometric view a machinery in accordance with the present invention.

It is therefore foreseen a frame inside of which the main sections are placed that distinguish its functioning.

The frame is formed by two lateral walls 2, opposed and distanced one from the other. The lateral walls rest on a support base 3 that serves as support for the components described below in detail and they are emerging vertically from such support base.

In this manner, an area of the machinery is delimited inside of which the sections necessary to complete an analysis of the slide are found, from the preparation of the slide until the analysis at the microscope with digitalization of the acquired images.

On top of the two lateral walls there are arranged two sliding tracks (4, 5), distanced one from the other. The tracks connect transversally the two lateral walls so first track 5 goes from an angle of a wall to the equivalent angle of the other wall in the high back area. Practically parallel to it is arranged second track 4. On first track 5 and second track 4 rests and slides the loading system 10, better described in detail below, and through which the slides on which the analysis is done are prepared/moved. More in detail, the track 5 is placed on a beam that connects longitudinally the two vertical walls in the back/high position and the same takes place on second track 4, which is parallel to first track 5 and on which the wheel support of the system 10 slides.

FIG. 1 shows in detail the wheel support in first track 5 and the same takes place in second track 4. In this way, the loading system translates in the direction X.

FIG. 1 shows the loading system 10 that results translatable in the direction Y and in the direction X and, in turn, foresees sections, mobile vertically, through which a slide can be collected, a cover slide can be arranged on the same and the slide can be prepared with the various liquids and serums. In this way, such system 10 is practically mobile inside the area of the machinery in question.

Figure 2:
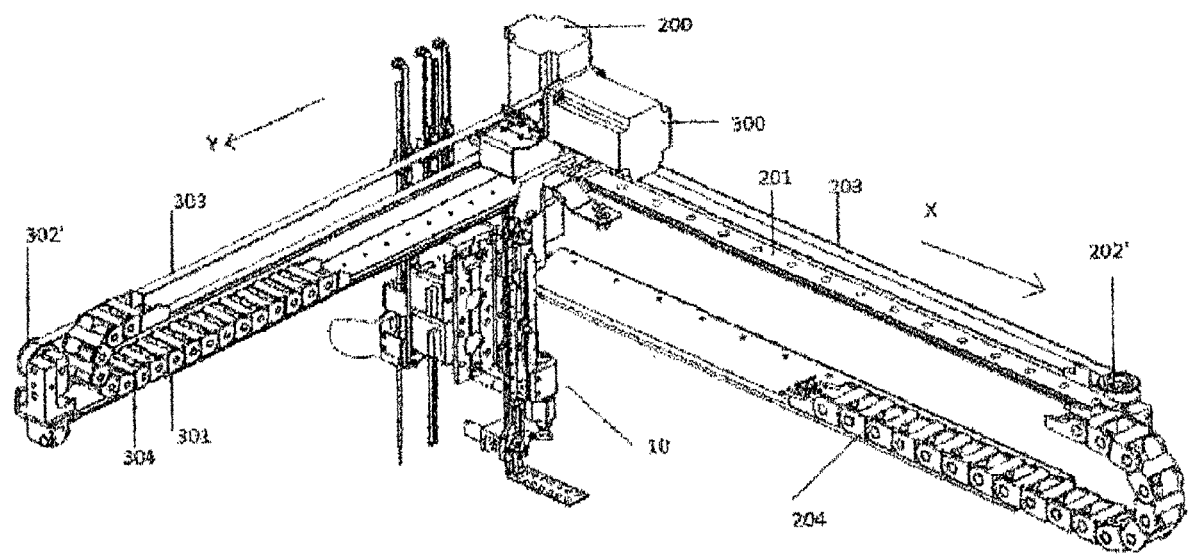
FIG. 2 and FIG. 3 show details relative to the translation system that allows the movement in the directions X and Y of the relative device that foresees the gripping pliers of the slide, the gripping sucker of the cover slide and the aspirating/application needles.

FIG. 2 better shows in detail the translation system in the direction Y and in the direction X that controls, as said, the movement of the loading system 10.

Figure 3:
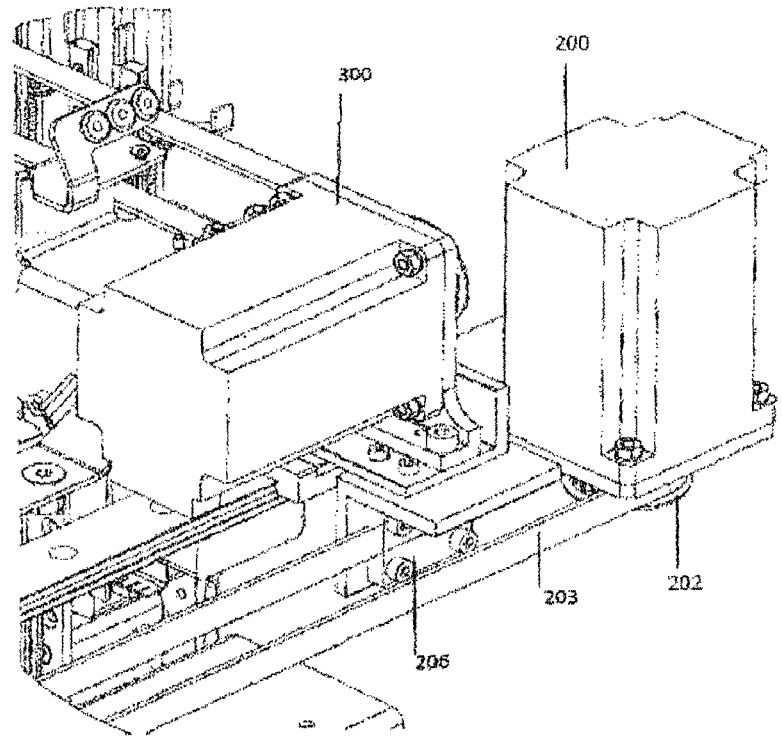

Two engines (200, 300) are therefore foreseen, one for the direction axis X and one for the direction axis Y, better highlighted also in FIG. 3.

As seen from FIG. 3, the engine 200 foresees a pulley 202 to which a movement belt 203 is connected, and the engine 300 foresees a pulley 302.

The engine 200 brings in rotation the pulley 202 that thus activates the belt 203.

The belt, of the closed-ring type, converges at an opposite pulley 202' and naturally the belt is adjustable in tension to the desired values, in accordance with well-known tensioning systems.

In this manner the pulley 202, through a rotation thereof, when activated by the engine 200 is started.

The belt is connected to a chain 204 (visible also in FIG. 1). The chain is simply a wire-holder and/or pipe-holder system in the sense that these are connected to it in such a way as to be compacted and to move together with all the group without creating particular encumbrance. To that aim, the chain 204 is connected to a fixed point on the frame and to a mobile point that translates along the direction X with the entire loading system.

As seen from the detail of FIG. 3, a constraint 206 binds all the loading system 10, included its translation axis along the direction Y and relative engine 300, in such a way that along the direction X all the system is moved integrally when the belt 203 goes in rotation. In this manner, all the block (that is loading system 10, relative track axis Y and engine 300) translates in the direction X, moving on the tracks (4, 5) and then the single loading system 10 can translate along the transversal track (described below) in the direction Y.

Naturally, the order of the movement is not limiting because, for example, there may be first a movement in direction Y and then in the direction X or vice-versa.

The translation in the direction Y takes place in the following manner.

Always with reference to FIG. 2 the sliding track 301 (the transversal one, perpendicular to sliding track 201) is therefore foreseen, to which the loading system 10 is linked slidingly, in turn connected to the belt 303. The belt 303 is activated thanks to the engine 200. Even in this case is present a wire-holder and/or pipe-holder chain 304 parallel to the axis Y with a fixed point on the axis Y and a mobile point that translates in direction Y with the loading system 10. The rotation of the belt 303 makes the entire loading system move in the direction Y along the transversal track.

Figure 4:
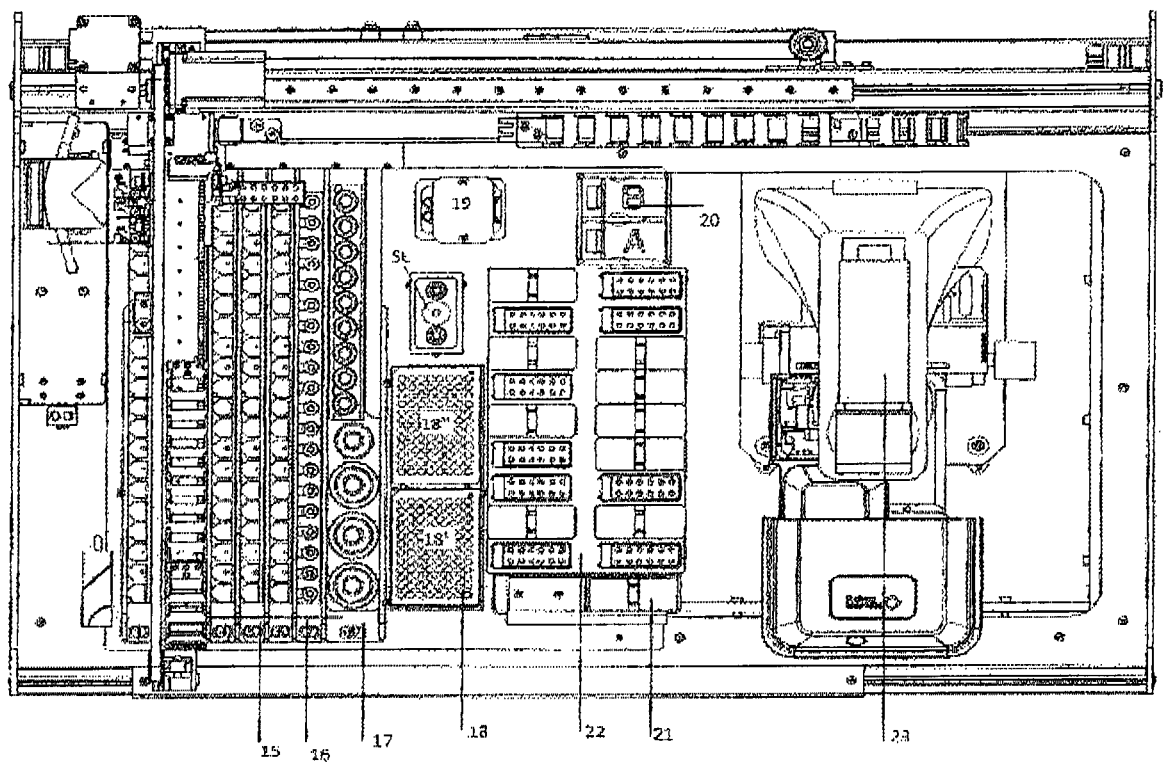
FIG. 4 shows a top view of the entire machinery.

FIG. 4 shows a top view of the present machinery in such a way as to highlight the other components.

Basically, different sections can be distinguished, each one suitable for a specific function.

With numbers (15, 16, 17) is distinguished in fact the lodging space of the preparations necessary for the preparation of the slides.

With number 15 the "Rack" of the samples has been indicated, which is a base of containment that foresees lodgings for the containers where the substances taken from the patients for the analysis are placed. Such containment bases are placed on rows parallel between them, and a detail of them is for example shown in FIG. 5. For example, both FIG. 1 and FIG. 2 show six rows in parallel and each row contains a containment base that foresees preferably 20 lodging seats for test tubes containing the relative samples. Naturally, a different number of rows can be foreseen.

In particular, the samples are inserted in test tubes of variable height and diameter (for example within a range of diameter between 11 mm-16 mm and with a height h between 130 and 160 mm). Each rack 15 (containment base 15) foresees lodging positions inside of which to position standing such test tubes (for example 20 positions).

The single rack is therefore a removable support furnished with such positions on which to arrange the test tubes and that can be inserted slidingly in its position as per FIG. 1 and FIG. 2 through specific tracks.

Figure 5:
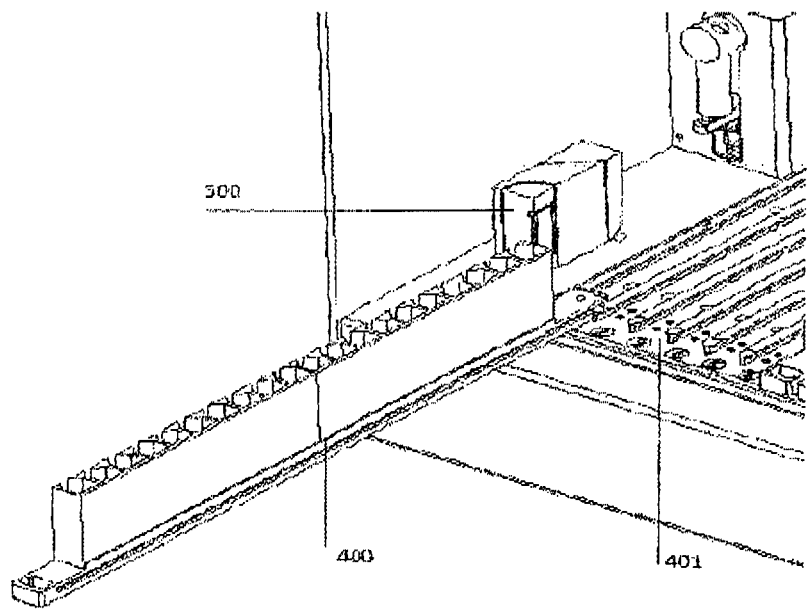
FIG. 5 shows a detail of the rack where the containers and a bar-code reader are positioned.

FIG. 5 better shows with structural detail this solution. In particular, such containment base is foreseen that forms the lodgings for the phials and arranged on a removable linear support 400. In this manner, the whole can be easily removed and inserted slidingly. Inside the machine are foreseen sliding insertion tracks 401 (in such a way that they can be removed, prepared and inserted) and a bar-code reader 500, better described in detail below.

The constructive solution described in FIG. 5 of the racks is valid for all the racks present in the described machinery.

With number 16 is instead indicated the rack of the positive and/or negative controls. Just for description completeness, by positive/negative controls are meant those controls applied on the windows instead of the sample of the patient and that permit to check if the processing practice of preparation of the slide has taken place in a correct way or not: in particular, the positive control has as output a certainly positive result, and vice-versa the negative control has as output a certainly negative result. In case a certainly positive control results negative or a certainly negative control results positive, then it means that the batch has not been executed in an adequate manner. This may have taken place (for example) due to the effects of degradation of the substrate applied on the window in the first case, while in the second case "Cross Contamination" effects may have taken place.

Normally, for each batch of single type of test produced (or at least at the beginning of the session during the working day) a positive control and a negative control are carried out in order to ensure the correct success of the test protocol.

With number 17, instead, the rack of the conjugates and of the diluents has been indicated, constituted preferably by nine conjugates, by a container of "mounting medium" and by three containers of dilution liquid.

With number 18, instead, the cuvettes have been indicated in a number comprised between two and three containers of 8×12 windows of dilution. The figure in the specific shows 2 containers 18' and 18".

The cuvettes are the areas where the deposition of the biological fluid of the patient takes place diluted according to what the test protocol requires with the diluent.

In other cases, the cuvette can serve as "support" for an intermediate passage.

With number 19, instead, the support is indicated in which the cover slides are arranged.

Figure 10:
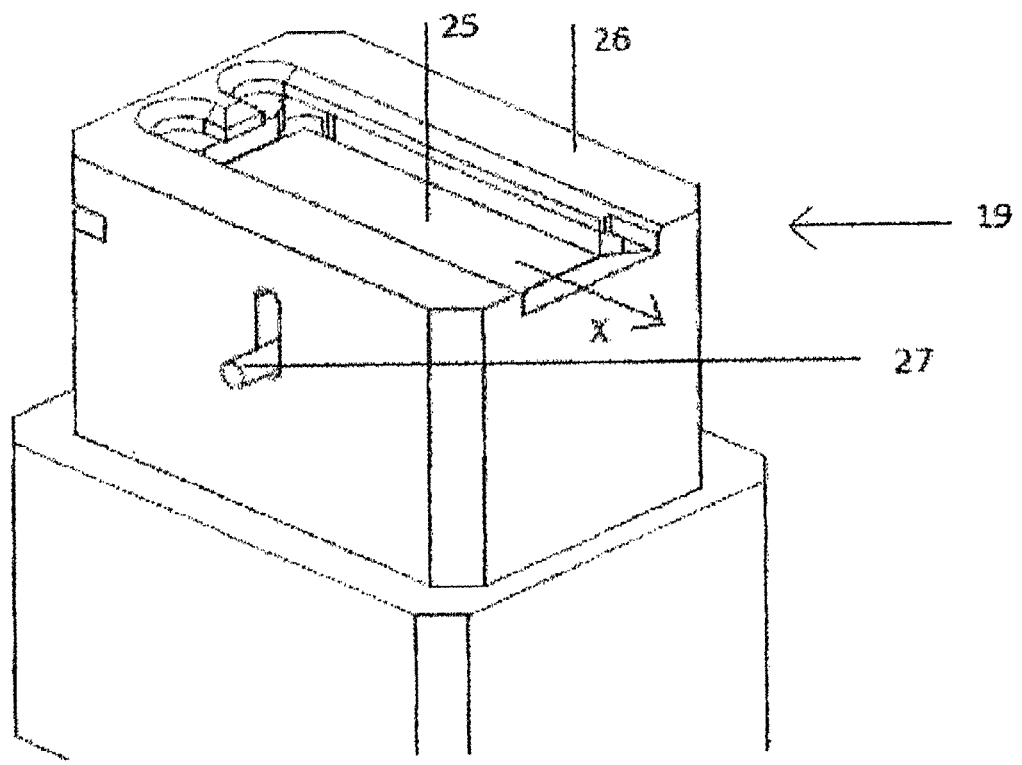
FIGS. 10 and 11 show a detail of the container of the cover slides.
Figure 11:
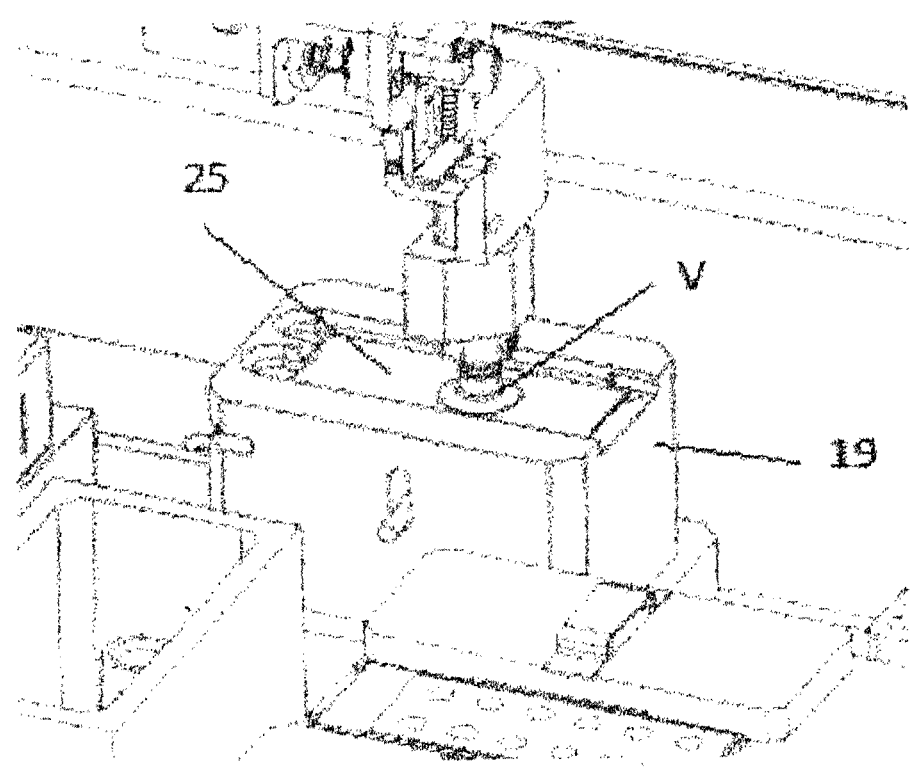

A detailed structural description of the support 19 is made in reference to FIG. 10.

The figure shows a container having a superior edge 26. The superior edge delimits an opening of a seat inside of which a support plane is arranged to hold the cover slides piled one on top of the other.

The support plane (not visible since covered by the slides 25 represented in FIG. 10) rests on a spring that tends to push the same (and therefore the slides) towards the superior edge 26. The support plane is impeded from exiting since the superior edge 26 serves as containment, appropriately delimiting the opening. FIG. 10 also shows a lever 27 connected to the support plane and which an operator can lower until a stop in the support plane is reached (for example, to make the loading of the cover slides). If it is then released, it ascends until when the cover slides beat against the edge 26. Operatively, as better described in the functioning phase, a sucker presses on the cover slide, grasping it and allowing the extraction thereof through a translation in the direction of the arrow X of FIG. 10. In this manner, the spring will take immediately the underlying cover slide in contact against the edge 26 ready to be collected.

Going back to FIG. 4, with the name (SL) is indicated a washing station that results interposed in a space comprised between the support 19 and the cuvette 18".

Figure 7:
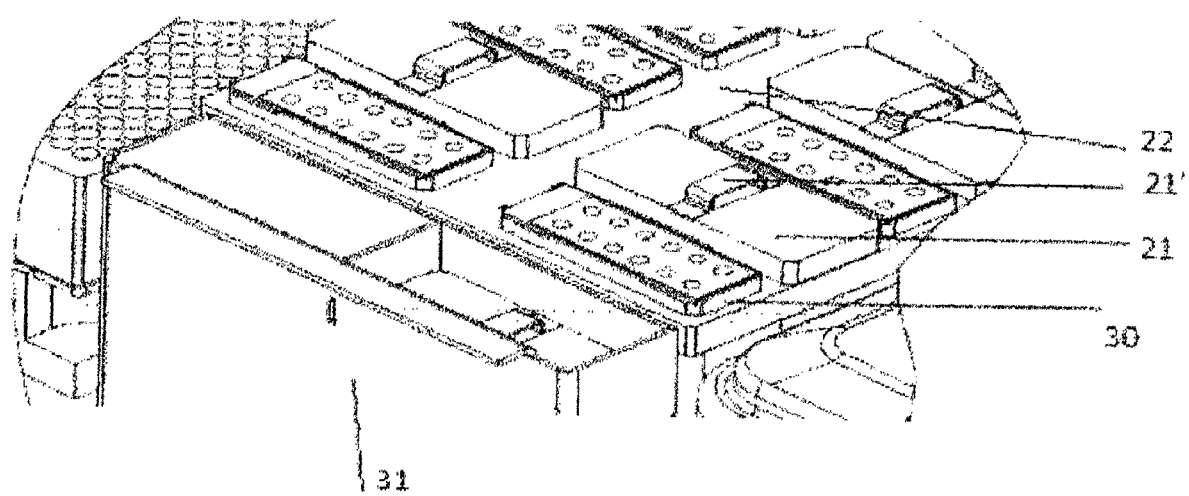
FIG. 7 shows a support plane on which the slides for the analysis are arranged.

Always in FIG. 4, and in the detail of FIG. 7, with number 22 is indicated the support base on which the slides are arranged.

A more specific detail is precisely shown in FIG. 7. On such support base the seats 30 are defined where the slide is placed and which are in the form of a containment frame.

Between a seat 30 and the other one, placed beside, a space is foreseen that can eventually allow (if necessary) a support of a cover 21 described below.

The cover foresees a gripping handle 21'. The size of the cover is such as to be able to be applied to cover the slide and the seat 30 on which such slide is placed.

Beside the base 22 a container 31 can be placed inside of which a pre-determined number of covers 21 is piled.

In use, therefore, the operator removes the slide from its package, takes the silica-gel contained in the wrapping (which limits the harmful effect of moisture on the slide) and positions it in the hollow or seat 30 arranged on the support plane. At this point it inserts the slide in said seat over the silica gel and applies a cover 21 by hand to cover the slide. The combined effect of the silica gel and of the cover optimizes the time of duration of the slide.

The machine, as described in detail below, executes automatically the removal of the cover at the right moment, after the pre-dilution phase of the samples, to proceed with the automatic preparation of the slide and its analysis.

The phase of arrangement of the slides on the plane 22 is made by hand and is facilitated by the fact that the plane 22 itself is removable from the machine (precisely to render easier to the operator the operation of application of the slides) to be then re-insertable in position inside the machinery. Also the container 31 is removable.

Normally, the phase of pre-dilution can make the machine employ even a couple of hours and in that sense it would be impossible to apply the slides before and leave (walk away system) because normally the start time of the substrate deterioration due to the moisture of the air is of about 15-30 min. In the current machines, therefore, the system is divided into two phases, the first one is of pre-dilution and subsequently the technician comes back and inserts the slides and the machine initiates the processing of the same. With the present machinery that is capable of removing automatically the cover to arrange it in the container 31, it is then possible to arrange the covers on the slides to avoid this second phase and thus loading the machine at the beginning. The covers should maintain a condition analogous to that of the slide in the own container, permitting to avoid the return of the lab technician.

In addition to the cover, an aspirating system can be integrated below the plane 22 that creates a vacuum inside the seats 30 in such a way as to inhibit further the effect of moisture on the deterioration of the slide.

Figure 6:
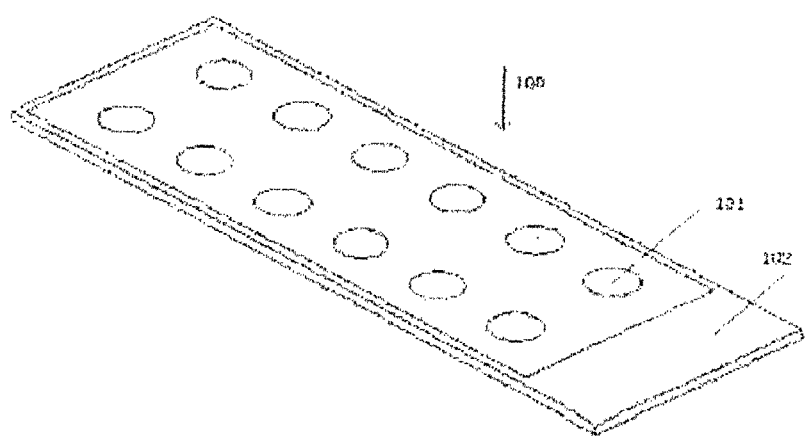
FIG. 6 shows an analysis slide.

FIG. 6 better shows in detail a slide 100, usable and of the standard type.

The slide foresees the substrate on which the windows 101 are arranged and foresees an area 102 free of windows to allow a mechanical gripping thereof and the movement thereof. The size and arrangement of the windows can vary on the basis of the type of slide.

The movement system of the slide and of its preparation is instead constituted by the system 10 introduced in FIG. 1 (the system translatable in the directions X and Y). It foresees:

Gripping pliers for the grasping and the movement of the slide;

A system of collection of the cover slide;

A system of aspirating/application needles of the serums on the slide.

Figure 8:
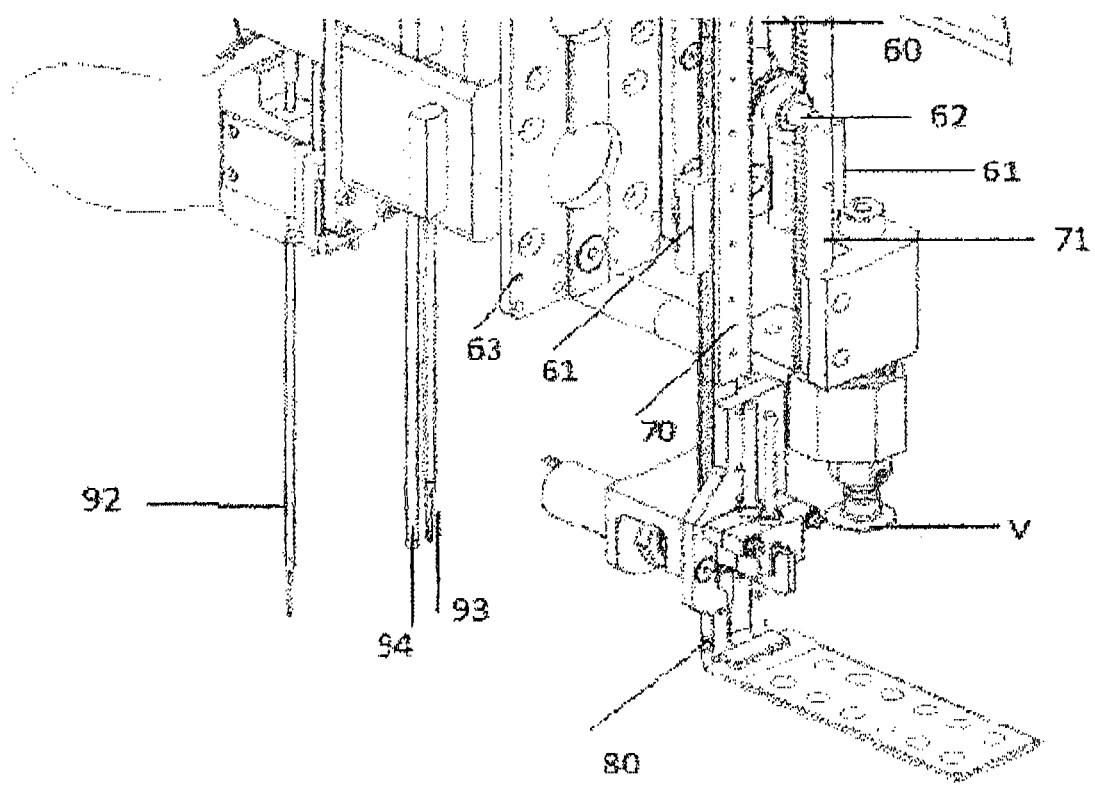
FIGS. 8, 8A, 9 show a constructive detail of the pliers.
Figure 8A:
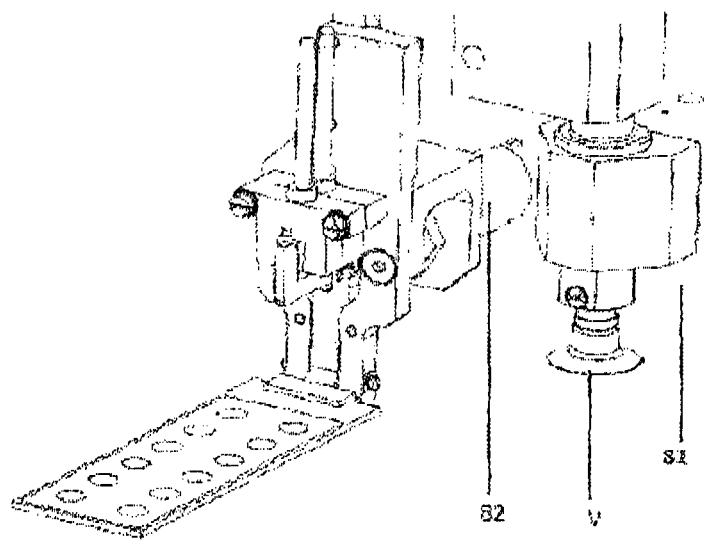
Figure 9:
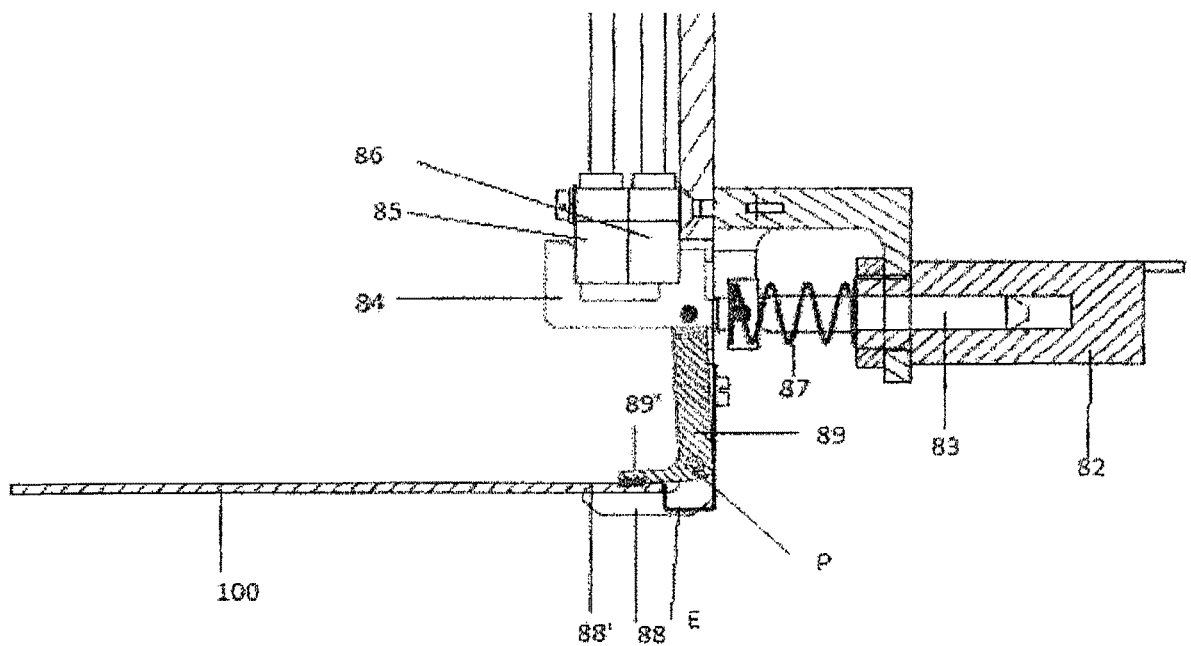

With reference to FIGS. 8, 8A and 9, these show constructive details relative to the gripping pliers.

FIG. 8 shows the entire loading system 10 where the gripping pliers, the removal/application system of the cover slide and the assembly of the aspirating needles result placed. As said, such entire loading system 10 is translatable in the directions X and Y through the tracks of FIG. 1 and the motors 200 and 300 and the transversal track.

It is therefore foreseen a first plate 60 on which two parallel sliding tracks 61 are arranged. On such two tracks are arranged, in a vertically sliding manner, two toothed bars (70, 71) (also called racks) which can be moved in their high/low vertical motion through a dented wheel 62.

Being just one the dented wheel that engages with the two bars, when the rotation is in a direction it happens that a bar lowers and the other one lifts in a synchronized manner and when the rotation direction changes then the lifting/lowering direction of the bars is also inverted (the bar that first lowered now lifts). A specific controller controls the rotation of the dented wheel 62 and therefore commands the exact quantity of lowering and lifting of the two dented bars.

To a dented bar (the bar 70) is connected the system 80 with gripping pliers of the slide.

At the end of the bar 71 is connected the system 81 of collection of the slide cover.

The pliers system 80 is described in detail in FIGS. 8A and 9.

In particular, a solenoid 82 is foreseen having inside it a sliding block 83 mounted slidingly. The sliding block, translatable in the longitudinal seat thereof of the solenoid, connects to a fork 84 on an end of the sliding block opposed to the one of the solenoid. The fork, which is therefore translatable on the basis of the translation of the sliding block, is configured in such a way as to obscure two sensors (85 and 86) or let them free.

Interposed between said fork 84 and the sliding block 83 a spring 87 is foreseen.

The gripping pliers, always shown in detail in FIG. 9, schematizes a slide 100, eventually grasped.

The pliers is made of two L-shaped parts, of which one is fixed (the part 88) and one is mobile (the part 89).

The mobile part is hinged to the fixed part through a hinging (P) so that the rotation of the part 89 with respect to the fixed part 88 causes a moving apart/drawing near of the flat gripping part 89' with respect to the fixed flat part 88'.

The flat part 89' can be provided with rubber or other material that favors the seal of the slide by friction following the grasping.

In the rest condition (without current) the spring 87 of the solenoid 82 pushes the pliers to be closed, that is the part 89' is rotated towards the part 88' as per FIG. 9. There are two possibilities, either the slide is present or it is absent. If the slide is absent, the fork 84 will be in such a position as to obscure only the first of the two position sensors (the sensor 86). The machine has therefore the information that is not present in the slide. If the slide is present, the rotation of the part 89' with respect to the part 88' will be such that both lights are free, therefore the machine has the information of the presence of the slide (exactly the condition of FIG. 9). Last, in order to take the slide it is necessary that the pliers open. In that case, the solenoid is excited and the sliding block is re-sucked inside the longitudinal seat of the solenoid, beating the force of the spring 87. In this manner, the pliers rotate and open, obscuring in this case only the second of the two sensors (the sensor 85) and giving the machine the information that the pliers are open. In order to have the slide in the right position a small elastic element can eventually also be foreseen that can eventually give also some energy to push the slide away if necessary.

Going on with the description of the collection system of the cover slide, this is constituted of a simple V-like sucker which, as per FIGS. 8 and 8A, is lowered on the slide until grasping it for its extraction.

Referring to FIG. 8, the lowering of the V-like sucker is obtained precisely with the translation downwards of the whole dented bar 71 on which the sucker is mounted. The same thing, naturally, is valid for the pliers 80.

Going on with the structural description of the invention, the system 10 foresees also needles for the aspirating/application of product. In particular, two precision needles (92, 93) and an aspirating needle 94 are foreseen. Such needles are mobile vertically and their exact position can be determined through specific capacitive sensor of liquid level reading.

Figure 12:
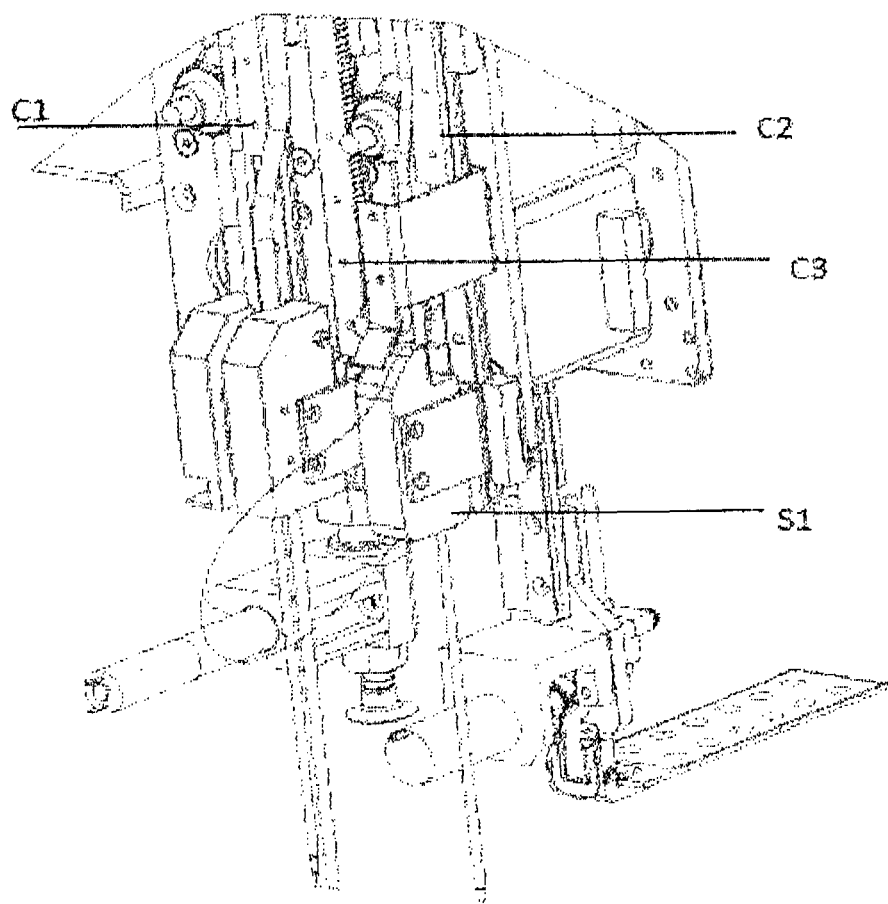
FIGS. 12 and 13 show constructive details relative to the lowering/lifting systems of the pliers, sucker and needles.
Figure 13:
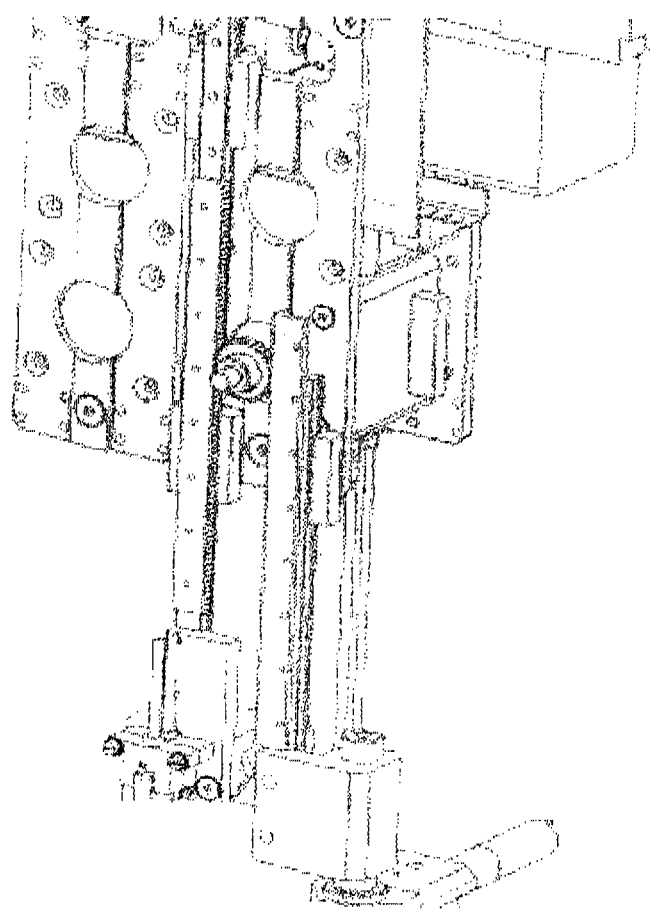

With reference to FIG. 12, on the opposite part to the two racks that command pliers and sucker, there are the racks through which the vertical movement of the needles activates.

In particular, the rack (C1) is commanded in translation through an own engine and own dented wheel in such a way as to lower the relative precision needle to which it is connected.

On the opposite part, the other rack (C2) lowers the other precision needle.

In the central part the rack (C3) commands the lowering/lifting of the aspirating needle.

A capacitive sensor (S1) for each needle (three needles as a whole in figure) is foreseen.

The position of the needle is therefore known always, since the position of the relative stepper engine is known that adjusts its movement. The capacitive sensor serves to know the position of the liquid: the needle is of metal, and therefore, when it meets the liquid, the overall capacity of the system (that is constantly monitored by the sensor) is varied and this is the information that the machine acquires to block the needle. At this point, the machine knows that the needle is slightly under the liquid surface (in some cases it is made to descend 1 mm for safety reasons) and the aspirating phase can initiate.

Naturally, a controller appropriately programmed manages automatically all the movements and the whole can be monitored from video by an operator.

Going back to FIG. 1 and to FIG. 4, the optical section 23 is highlighted where the optical microscope is arranged on which the slide is placed at the moment in which the images must be acquired, once all the process of preparation of the slide has been completed by the machine cycle and the result of the test has been completed.

On the machine is present a bar-code reader 500 (see FIG. 5) that guarantees the acquisition of the information on the data of the test tubes in an automatic manner.

The bar-coded elements are: a) test tubes; b) rack.

In particular, on the rack there are two types of information: b1) position of the test tube and b2) presence or absence of the test tube, while on the test tube itself there is a bar-code that identifies the subject to which the exam is done.

The system functions in this manner: the operator puts the rack in the loading position as per FIG. 5 and a magnetic sensor (not represented in figure for simplicity reasons) reads that the rack is present and recognizes the insertion row, for example the row numbered in FIG. 5 with number 401. At this point, the bar code reader focuses on said row and the operator can complete the insertion of the rack, while the bar code reader will read the various bar codes during the insertion.

In the rack for each position there is a barcode identifying a number (therefore there will be the numbers 1, 2, 3 . . . n numbers) and that identifies the test tube. Further, where the test tube is inserted normally there is another bar code with the writing "EMPTY" and that identifies the empty condition. Let's suppose that we insert the rack completely empty, then the reader will read: 1, EMPTY, 2, EMPTY, 3, EMPTY, . . . .

In this manner, the machine knows that at the position 1 there is nothing and so on.

Let's suppose now there are test tubes with their bar codes; they hide the bar code with the writing EMPTY, and the reader will read: 1, RED, 2 WHITE, 3 GREEN, etc.

In this manner, on the specific rack is known for each position if a test tube is present or not, and if it is to whom it belongs.

There is a last possibility, which is that the bar code of a test tube is damaged (the hypothesis that the bar codes are damaged or missing on the rack is not considered in this routine) or missing, then we will read:

1, RED, 2, 3, GREEN, . . . .

The reading of two subsequent numbers 2, 3 gives the information to the machine that the insertion is wrong; the machine warns the operator, who will have to check and eventually insert the codes manually.

At the end we will have the information that will link univocally the sample of the patient to a position in the machine.

It is further foreseen a second bar code reader to be applied directly on the loading system 10. Said bar code reader is suitable for the reading of bi-dimensional bar codes that can be present on the slides. In that case, through the movement XY of the machine, the bar code reader is brought in proximity of the slide and the type of slide used is checked, after the removal of the cover if it is not transparent.

Figure 14:
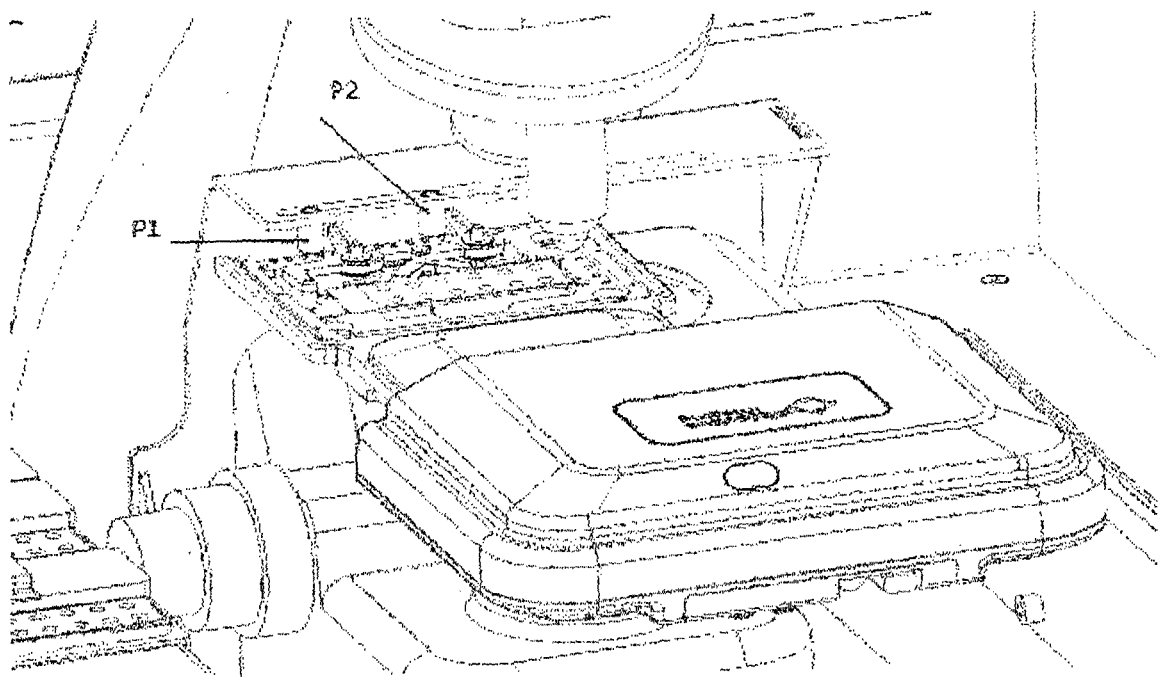
FIGS. 14 and 15 both represent details relative to the section of the microscope.

FIG. 14, last, shows greatly in detail the optical station in which it is foreseen, as said, the optical microscope that acquires the images. The optical microscope is provided with a mobile board in the directions X, Y and Z to adjust the acquisition of the images.

Figure 15:
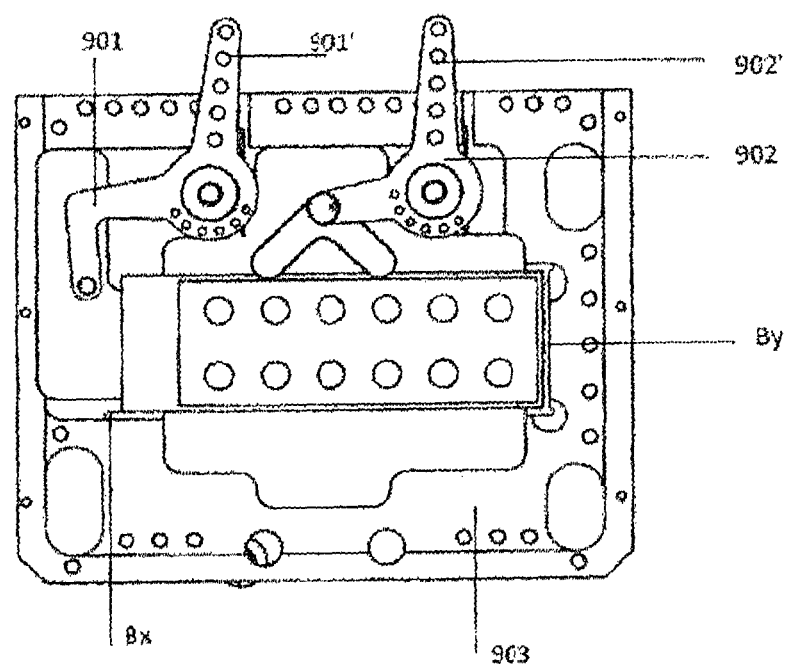

FIG. 15 better shows in detail a fixing system of the slide below the microscope and with a blocking system that creates a precise reference, so as to eliminate totally the risks of insertions in wrong positions.

A support plane 903 is therefore foreseen which is integral to the motorized board of the microscope. The support plane 903 forms a cradle for holding the slide and is provided with an end stop (By) and an end stop (Bx).

FIG. 14 shows two fixed pins (P1, P2) that are integral to a part of the fixed structure of the machinery. Two pins (901, 902) are instead mounted integrally and rotatably with respect to the board 903 and both foresee a return spring that maintains them always in the condition of stop on the slide. The pin 901 has two arms so as to assume an L shape and on the end of an arm there is a further appendix. The pin 902 is L-shaped and on an end a "V"-shaped element is hinged. The return springs that tend to bring these two pins in the position of FIG. 15 serve to push the slide against the stops Bx and By in such a way as to freeze a position that is always univocal for each slide and therefore always the same, without the possibility of different positionings.

This ensures a correct acquisition of the images.

The pliers therefore put the slide on the board 903 when the board is translated in such a position that the fixed pins (P1, P2) go in contact and maintain in rotated position the pins 901 and 902 so as to allow the pliers to lean the slide in a generic position in which the sides of the same do not beat against the stops Bx and By. The pins act on the sides 901' and 902', maintaining the pins in a rotated position. Once the slide has been leaned, then the board translates, moving apart from the fixed pins (P1, P2) and at this point the pins 901 and 902 rotate against the slide, bringing it to a stop in the position of FIG. 15.

The motorized board completes its movement bringing the slide under the microscope in direction X and Y and the acquisitions of the single windows are thus made through a "collage" of images. The microscope can have one or more lenses mounted with appropriate magnification to do the analysis (for example 20.times. and 40.times.).

The images, as known, are then rendered available in electronic format, eventually browsable also on the Internet from remote.

Figure 16:
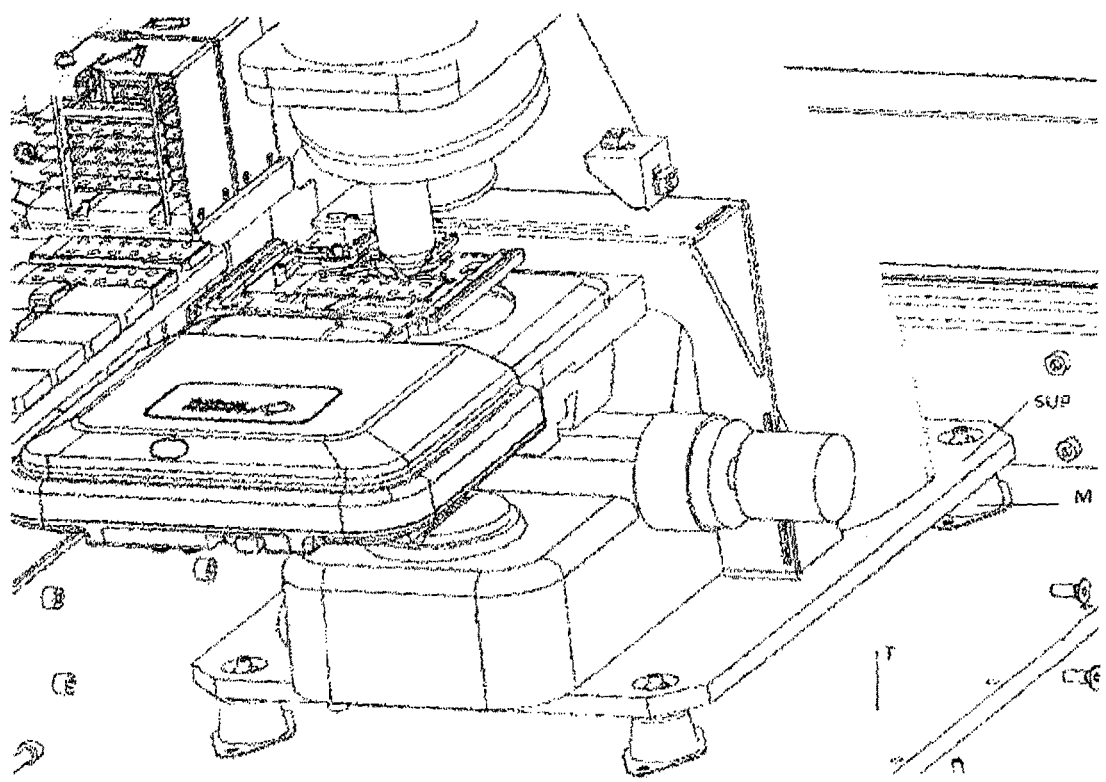
FIG. 16 illustrates a type of anchorage of the microscope to the floor.
Figure 17:
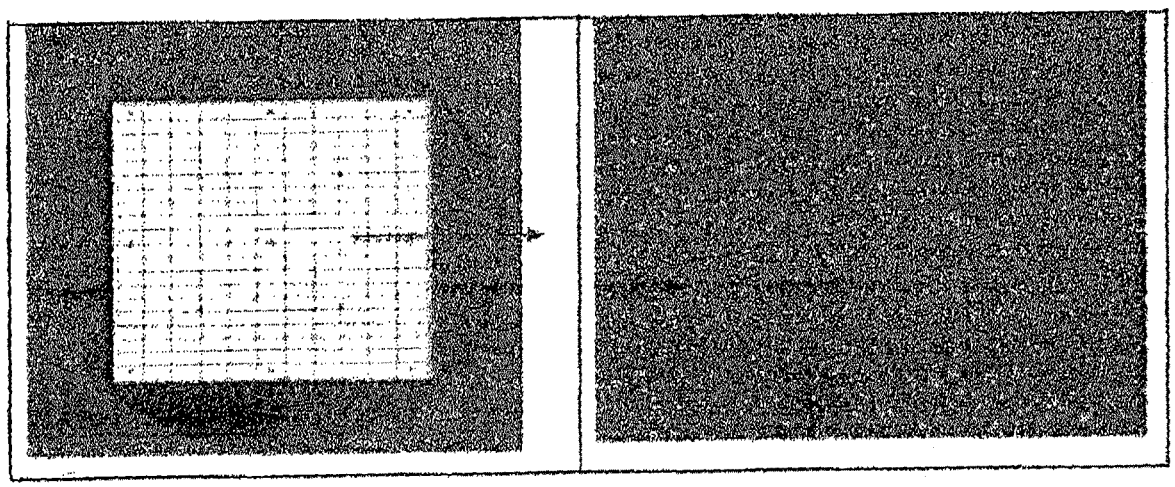
FIGS. 17 and 18 both represent the process of digitalization of a window with the creation of the virtual microscope.
Figure 18:
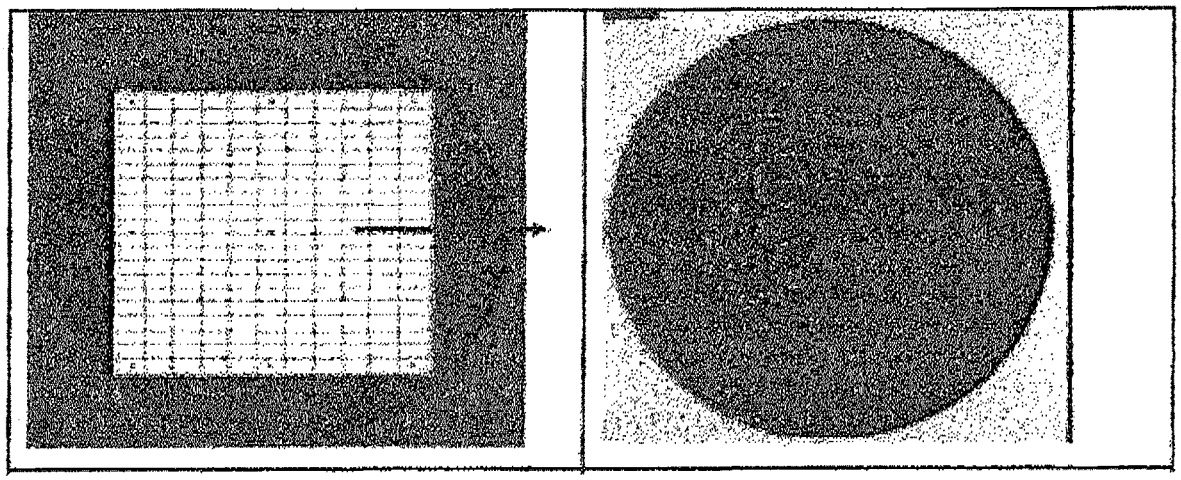

FIG. 16 shows in detail a particular type of anchorage of the microscope to the flooring, so as to reduce to the minimum eventual vibrations that could disturb the acquisition of the images.

In particular, the figure highlights part of the frame T on which dampeners M (for example springs, in figure in a number of four) are arranged and on which the support (SUP) of the microscope is fixed. Naturally, the choice of four shock absorbers placed at the angles allows to dampen more efficiently the various vibrations.

Having described the invention from the structural point of view, we now pass onto a description of use and functioning.

At the start of the process, the operator initiates to load on the machinery racks of the samples that contain the samples of the patients in the test tubes. As per FIG. 5, the operator draws the rack near the own column of insertion and engages the front part of the same. A sensor recognizes the position and activates the bar code reader to guarantee the correct reading of the codes contained on the samples and a LED light illuminates with a fixed light to warn about the correct codification of the column.

As described in detail above, the rack foresees for each position a series of pieces of information, among which the position (1, 2, . . . n) of the sample or if the test tube is in position in the rack. In the case of abnormal positions or loadings the processor warns through a sound signal, with the blinking of the LED light of the column in question and with information on video and the operator must re-set a condition of correctness. Once the rack of the samples has been inserted correctly, a signal on video warns that the column has been correctly inserted. The operation must be repeated for the various racks that can be introduced in the machine. Likewise, in the phase of introduction of the controls and of the conjugates the insertion rack is engaged in the relative row, the machine warns about the correct arrangement of the BCR (Barcode reader) and subsequently the reading of the codes on the containers takes place.

Once the fluids of the patients have been introduced, the containers of the cuvettes and the slides are introduced. The slides are inserted in the seats 30 of the support plane 22 which is removable from the machine. The operator removes the plane and loads it with the slides, once these have been removed from the own container. They are subsequently covered, always by hand by the operator, with the cover 21.

Subsequently, the support 19 of the cover slides must be introduced.

It has to be further checked the presence of the washing well of the needles, the two parking racks of the cover slips 21, and the slides 100.

The operator associates the window of the slide to the sample to be tested through the display screen interface of the machinery and the machine, following the definition of the tests to be carried out, checks if there are enough components (samples, dilution liquids, controls, slides, etc.) on the worktop to make the batch. Having said information the operator must, if necessary, make the due modifications following the procedures indicated by the display screen.

Further, the machine checks the levels of liquid in the washer, buffer and "waste" tanks and on the basis of the condition of overvacuum or overfill warns about the necessary top-ups/unloads to be carried out; alternatively, the process is ready for being started.

The first phase is relative to the preparation of the diluted samples, which is the pre-dilution phase.

In said phase the robot moves the loading system 10 over the dilution liquid, moving the precision needle/s that take/s the dilution liquid in the necessary quantity (microliters) for the activity to be performed.

Subsequently, the robot moves over the samples and the precision needle/s take/s the sample/s in the necessary quantity (microliters) for the dilution. In order to avoid contamination between the system liquid, the dilution liquid and the sample, every time the present hydraulic circuit (the one that generates aspiration/push in the needles) generates an air-gap between the columns of liquid; said air-gap must be as small as possible to avoid the generation of an excessively elastic column of fluid with loss of precision during the deliveries; nevertheless, it must be big enough as to avoid the contamination of a fluid with the fluid of system.

The air gap is an air bubble that has the function of avoiding mixtures between the liquids in question. If, for example, no mixtures must be obtained between the dilution liquid and the serum of the patient before being unloaded in the cuvettes, then such air gap is generated that separates the two fluids.

It is also to be noted that in order to make correct liquid aspirations the needle/s follow/s a precise movement routine: in a first phase they descend until identifying the surface of the liquid through the sensors S1. Thanks to this operation the height at which the needle has to be initially arranged is registered in the movement management programme, subsequently the needle makes a second descent and is placed at a pre-determined height (about one millimeter) under the level of the free liquid surface and from this moment, and during the aspirating phase, known a priori the size of the containers, the needle will move following the variation in height of the free liquid surface. All these operations have the aim of avoiding the formation of air bubbles in the column of fluid sucked that would affect the result of the dilution. The detention of the liquid level is carried out through the sensor S1 studied on the basis of the geometries of masses of the machine to guarantee maximum resolution inside the electromagnetic assembly in question; eventually, it is also possible to use bubble sensors suitable for checking the presence of liquid bubbles in the routings in order to avoid abnormal distributions of the fluids.

Following this phase the precision needle/s is/are placed in correspondence of the cuvettes by the robot and once the correct height has been reached they dispense the diluted sample in a single option: in this phase the mixture of the fluid is obtained through the vigorous dispensation carried out thanks to the hydraulic circuit and in particular to the precision pump. If wanted, it is also possible to carry out subsequent re-aspiration and re-injection of the diluted, always using the safety air-gaps to which reference has already been made.

The operation of dilution can be carried out in a single passage, for example if we want to dilute 1:40 a sample will take place as follows (in a merely indicative manner): an air gap is generated in the column of the system liquid (ex. 15 microliters), subsequently 390 microliters are taken of diluting liquid and a new air gap is generated (ex. 15 microliters); last, 10 microliters of sample are collected and a further air gap is created with the function of "anti-drop object", which is a vacuum to avoid the dripping during the phases of movement over the worktop. The column thus produced is injected in the respective cuvette. In other cases, the operation of dilution can be carried out in more steps, which means a pre-dilution is first done in a cuvette and subsequently the same pre-diluted is used for a further dilution. This procedure guarantees a use of less quantity of diluting liquid even if it is somehow longer in terms of time.

Once the preparation of a diluted sample has been executed, the needle/s are brought over a washing position: it is constituted by cylindrical chambers where the needle is inserted; subsequently, through the washing and system fluid (wash) the precision needles initiate to make said liquid circulate, which washes both internally (in a direct manner) and externally (inside the cylindrical chamber that is filled) the needle itself; the passage of the fluid must be vigorous enough, for this reason it is necessary to use as feeding system a peristaltic pump instead of precision pumps. Once the needles have been washed, the phase of deposition on the sample is carried out.

Such preliminary operation described can require some hours. Thanks to the use of said cover 21, the slides can be loaded at the beginning, which is before the operator starts such pre-dilution process, so that from that moment onwards the process results totally automated.

At this point, the processor moves the loading system 10 on the slide to prepare and, through the gripping pliers 80 hooks and lifts the cover 21 present on each slide. The slide is deposited in the storage room 31. In this phase a further bar code reader, placed on the loading system 10, carries out the reading of the bar code contained on the slide.

Alternatively, the reading can be made through the cover 21, if this is foreseen transparent, at the beginning of the process.

The precision needle/s are positioned through the loading system 10 on the relative cuvettes where the diluted sample is placed, with a procedure of vertical registration analogous to the one previously described. The needle/s are positioned under the free liquid surface and initiate the aspiration (after a safety air gap has been created as usual). Subsequently, an air gap anti-drop object is created and the needle/s move/s, last, over the window/s on which the application of the sample must be made and proceed with the deposition (microliters) according to what has been established by the test protocol.

Once the operation has been terminated, the needles are washed. In this case, the washing can be quite contained (in the hypothesis of having many windows on the same slide), foreseeing a more accurate cleaning at the end of the preparation of the slide. We highlight in this case some important considerations: 1) the software of the machinery manages in this phase the acquisition of the information at the moment of the start of the test on each single window; in fact, we cannot exceed the threshold of 30 minutes of incubation to avoid the formation of non-specific links on the substrate of the window; 2) in some cases some windows are used to check that the method of the test is executed correctly, in such case instead of the diluted sample the needle sucks controls (positive/negative).

Once the period of incubation has been terminated, the phase of washing of the slide is carried out: the loading system 10 is positioned with the precision/dispensation needle and with the aspiration needle over each single window and a procedure of washing of the same is started. Said procedure can follow different washing philosophies, on the basis also of the type of substrate.

An example of washing can be that at a continuous flow on single window until a certain quantity (microliters) of "buffer" is made to pass on the same window; in this phase the dispensation needle sends the fluid on the window through the peristaltic pump in a continuous manner and the aspirating needle, through a membrane pump (for example), recalls the fluid in the waste tank. Another methodology can be that of applying a drop and sucking, and repeating the operation many times, either remaining still on the same window, or moving from window in window. The techniques in question are generally finalized on the experiential base on the basis of the types of substrate, and of some process parameters (time, type of buffer, etc., and last but not least the size of the window). The windows can in fact have different shapes and sizes and in order to meet the need of quick washings the relative position of the dispensation and aspirating needle can be varied so as to be able to cover directly both small windows and big windows with optimal distances for the washing. For some types of windows it is necessary to carry out the washing with a movement that sweeps continuously the length of the window.

Once the washing phase of the slide has been terminated and after the washing of the needles on each single window, a drop of system liquid is deposited. This has the function of stopping the proceeding of the formation of non-specific links until the start of the second phase; the maximum limit of permanence of the liquid is of about 15 minutes.

It is to be highlighted that, in addition to the washing of the dispensation needles, in case also the aspirating needle is used, this last one must also be washed. In order to do such operation the needle must be deposited over the cylindrical washing well and it must carry out the aspiration, while a precision needle delivers the washing liquid: in this case the direct washing is that of the external surface of the needle during the aspirating phase inside the window, while the indirect cleaning phase is that relative to the internal surface of the aspirating needle.

Subsequently, the precision needles remove the drops of protection and proceed with the application of the specific conjugates for the test. In order to carry out this operation the procedure is the following: the loading system 10 is placed over the containers of the conjugates, the needle/s is/are positioned under the free liquid surface (after a first phase of identification of the height of said free surface) and initiate the aspiration (after a safety air gap has been created as usual). Subsequently, an air gap anti-drop is created; the needle/s move/s, last, over the window/s on which the application of the sample must be made and proceed with the deposition (microliters) according to what has been established by the test protocol.

Afterwards, the incubation phase of 30 minutes is carried out, analogous to the preceding phase. Once the incubation period has been terminated, the washing phase of the slide is carried out: the loading system 10 is positioned with the precision/dispensation needle and with the aspirating needle over each single window and the washing procedure of the same starts. Said procedure can follow different washing philosophies, as first seen. Once the washing phase of the slide has been terminated, and after the cleaning of the needles on each single window, a drop of system liquid is deposited. This has the function of stopping the proceeding of the formation of non-specific links until the start of the third phase; the maximum limit of permanence of the liquid is of about 15 minutes.

The third phase consists of the application of the assembly liquid and of the cover slide. A precision needle is positioned over the container of the mounting medium, a container that foresees a particular septum membrane to make the needle enter and exit and at the same time reduce the evaporation phenomenon of the mounting medium if left exposed to the air. The needle makes a first descent phase with which it checks the height of the free surface of the assembly liquid; the second descent takes place some millimeters below the free surface and during the aspiration (after the generation of an adequate air gap) the needle descends in synchrony with the same free surface. Subsequently, an air gap is left with the function of anti-drop and the needle is positioned in proximity of the windows. The aspirating needle in such phase sucks the protective humidifying drops previously left and subsequently the deposition of the assembly liquid takes place by the precision needle. Such deposition is controlled by parameters such as the speed of delivery of the fluid that guarantee the avoidance of the forming of air bubbles in the same assembly means.

At the end of said operation, the needle cleans the exceeding mounting medium in the washing well. This phase must take place thanks to the movement of the end effector through the movement robot over the same well. After the cleaning phase the needle does a thorough cleaning to remove the residues of mounting medium through the system liquid or washer.

Subsequently, the loading system 10 is brought above the container of cover slides and lowers the sucker (V) on a cover slide which is removed from the support 19. Thanks to a sensor the correct grip of the component is actually checked. Such grip is checked through an appropriate fiber optic sensor that is capable of checking visually the grip of the slide, checking the refraction or not of light thereof.

Afterwards, the cover slide is brought over the slide to protect through the appropriate translation of the loading system 10.

Subsequently, the cover slide is applied on the slide. Also in this case the descent parameters are controlled in such a way as to render absolutely safe the support phase to solve the breakage of the cover slide and the formation of bubbles in the drops of assembly liquid.

The slide at this point is ready to be placed under the microscope. The loading system 10, with the pliers 80, takes the slide in the area designated for the grip and takes it over the movable board of the microscope. Such board permits the deposition of the slide and subsequently the loading system moves, disengaging the grip, and the board moves from the parking position, permitting the two pushers (901, 902) to apply on the two sides of the slide a force enough to maintain the same still during the scanning. In this case, it needs to be highlighted that the force applied must be correctly calculated in the project phase so as to avoid that the slide is straight, acquiring a posture of plane not parallel to the objective. It starts then the scanning phase of the window, the acquisition of the details of the image and the reconstruction of the same at software level. The image of the window is therefore acquired and at disposal for the relative analysis, as better described in detail below.

At this point the loading system 10 can operate removing the slide, the board of the microscope moves in the parking position, the two pushers disengage and the appropriate utensil contained on the loading system 10 takes the slide. The loading system moves in the parking area of the slide in output from the process and operates the final unload: once the slide has been deposited (with cover slide) the process can be considered concluded.

Naturally, the machinery processes many slides together; the constraints of incubation time per single window, of maximum time with humidifying, and of duration of the single processing phase imply a complex processed scheduling of the machinery, with a phase of preparation of the diluted samples that is done as initial phase of the process: in all the cases the machinery presents as a "walk away" machine, and once loaded the operator is free to move away; further, if the procedure is interrupted for any reason (feeding interruption, cover opening, etc.), the system re-calculates in virtue of the new data in possession the new processing strategy of the process for trying to save as many tests as possible or on the basis of priority orders introduced at the beginning of the analysis.

It is to be noted that in the description given the microscope belongs to the same assembly of preparation of the slides; in such case the scanning phase of a slide could take place in parallel to the scanning phase of another slide.

For this reason the loading system 10 that operates the movement of the system liquids can operate independently from the microscope. Nevertheless, is known the sensitivity of the microscope to the vibrations and to guarantee a correct execution of the scanning, it is necessary to uncouple the microscope from the rest of the machine. This, as described already in FIG. 16, is done by putting the microscope on appropriate supports and over an anchorage plane whose mass is calculated in order to reduce the vibrations that the alternating force (vibrations introduced by the engines and accelerating and braking phases of the inertial masses) introduced are reduced as much as possible. In other terms in a first approximation, the system is schematized as a system of two masses (support plane and microscope) connected by a dampening spring system and with alternating forces introduced by the movement of the "anchorage flooring" to the machine. The aim is to render minimum the movement of the second mass (the microscope).

Going further into the detail of the acquisition of the images, the microscope is controlled by specific software in such a way as to operate in the following manner.

For each slide the microscope, provided with telecamera and motorized board controlled by specific software, makes a first acquisition at low magnification (for example 20.times.) on pre-defined positions of the slide in such a way as to find the focus value of reference, therefore makes a procedure of auto-adjustment of the light and of re-focalization at high magnification on the slide, on each point of a pre-defined grill. In particular, it acquires a series of acquisitions at various quotas in such a way as to calculate the correct focus and starting from a quota of acquisition that is that obtained at low magnification.

Figure 19:
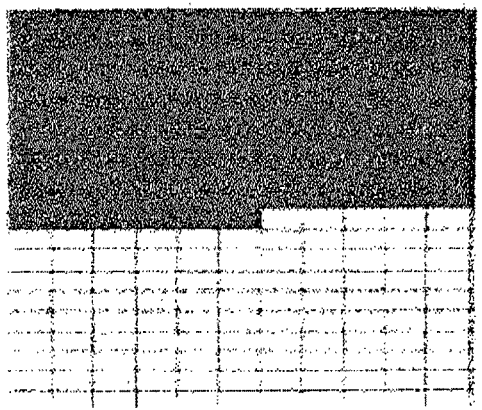
FIG. 19 represents how the images are acquired in the window for the reconstruction of the virtual microscope.

At the end of this procedure, the apparatus starts the acquisition of an assembly of contiguous fields at high magnification to realize the digitalization of the entire window through a technique called "mosaicing", with the board that moves in an incremental manner in a grill of adjacent areas defined by different coordinates X, Y, and the predictive focus value obtained with the procedure described previously (see FIG. 19). The final image of the slide is obtained by reconstruction of the mosaic type, assembling the images of the scanned adjacent areas, with a small horizontal and vertical overlapping on which the so-called Linear Blending technique is applied, so as to eliminate the discontinuities between the adjacent areas. The image thus recomposed is, last, compressed using a standard and known technique, jpeg2000. The visualization of the images takes place according to the known technique of the virtual microscope.

Such procedure is, for example, described in European patent application EP2587296 to which reference is made and here considered entirely included in the present text for reference.

As for the analysis of the digitalized images, a discrimination between positive and negative samples is done during the acquisition of the slide on the basis of techniques that identify the cells and evaluate the fluorescent intensity thereof. The overall intensity value of the cells of the window is compared to a curve of discrimination and in order to determine if the window is positive, negative or uncertain two pre-defined thresholds are used. The recognition of the cellular pattern is done with an algorithm of analysis that processes the images captured so as to distinguish the cells of interest from the surrounding background using threshold techniques and calculating for each single cell an assembly of morphological and dimensional parameters. These are used by a classifier based on the known technique "Support Vector Machine", a supervised learning method that allows to minimize the errors made by the operator during the recognition of the cellular pattern.

Ultimately, the present machinery, coupled, naturally, to a PC with a dedicated software, controls and makes:

All the movements of the system;

The correct execution of preparation of the slides following the biological protocol defined for each test. An algorithm (scheduler) calculates on the basis of the tests the single consecutive operations that the machinery must execute in such a way as to guarantee a correct preparation of the slides and the reduction of the preparation times without altering the quality of the preparation to be read at the microscope;

The creation of the virtual microscope of each window present in the slide. The software acquires contiguous images of each window in such a way as to cover entirely the area of the window reconstructed via software, recomposing them as a single image browsable through mosaicing techniques. If the operator desires to re-evaluate the window he can use the virtual microscope on any computer that offers anyway the complete vision of the slide at different magnifications.

The analysis of the images to furnish an automatic response of diagnosis for each test. The software analyzes each image of the window identifying the cells, evaluating the degree of fluorescent intensity thereof from which to obtain a positivity response to the test and the type of cells (pattern);

The saving on saving units of the digital slides.

In particular, a software is foreseen for the scheduling of the movements of the mobile group (10), respecting the biological protocols of preparation of the slides.

A software for the digitalization of the slides and visualization through virtual microscope is further foreseen.

A software dedicated to the visualization of the digital slides from remote positions (Intranet/Internet).

A software of image analysis for the quantification of the level of fluorescent intensity and of the cellular form.

Once the test has been concluded the machinery is capable of indicating a positivity response to each test done, identifying also the cellular pattern.

The invention claimed is:

1. A machine for preparation and analysis of one or more slides for a biological material according to an immunofluorescence technique, comprising:
   a loading station of one or more containers for holding test liquids and product samples;
   a positioning station of one or more slides comprising a support base provided with a plurality of seats each configured to hold one of the one or more slides, each seat having a base and a containment frame configured to hold one slide, the positioning station being removable from the machine;
   a containment station of one or more first slide covers;
   an analysis station comprising a microscope for acquisition of one or more digital images at one or more magnifications;
   one or more second slide covers being sized to cover the one slide arranged in one of the seats,
   wherein each of the one or more second slide covers has a top surface, provided with a gripping handle, and lateral walls extending orthogonally from the top surface in a direction opposite to the gripping handle, each of the one or more second slide covers being rectangular in shape and being sized to enclose within, in a volume defined by the top surface and the lateral walls, the containment frame and the one slide disposed within the containment frame, each seat receiving silica gel and the one slide on the silica gel, so as to cause a combined effect of the one or more second slide covers with the silica gel that reduces deterioration time of substrates of the slides;
   a container holding the one or more second slide covers, the container being removable; and
   a loading system, mobile along perpendicular directions inside an entire area defined by the machine, the loading system removing one of the second slide covers from one of the slides positioned in one of the seats after pre-dilution of the product samples has been completed, and arranging the removed second slide covers inside the container,
   wherein the loading system comprises,
   a gripping device, configured to collect the one of the second slide covers and to deposit the one of the second slide covers in the container, the gripping device being further configured to carry the one of the one or more slides coupled with one of the first slide covers from the one of the seats to the microscope;
   a suction device, configured to collect the one of the one of the first slide covers from the containment station and to deposit the one of the first slide covers on the one of the one or more slides positioned in the one of the seats, and
   one or more aspirating/application needles of a liquid, the gripping device, the suction device, and the one or more aspirating/application needles being jointly mobile along the perpendicular directions,
   wherein the loading system is further configured to move through the loading, positioning, containment, and analysis stations to prepare the one or more slides according to a pre-defined protocol while leaving the slides on the support base, and, after said preparation of the one or more slides, move the one or more slides to the analysis station for the acquisition of the one or more digital images, and
   wherein the loading system is mobile along the perpendicular directions by sliding along perpendicular sliding tracks disposed in an upper portion of the machine.

2. The machine of claim 1, wherein the containment frames of the seats extend upwardly from the support base, the containment frames being spaced from one another by space distances, the one or more second slide covers extending over the containment frames and into the space distances.

3. The machine of claim 1, wherein the one or more first slide covers are transparent.

4. The machine of claim 1, wherein the machine is configured to create a vacuum condition inside the seats, thereby inhibiting deterioration of the slide due to moisture.

5. The machine of claim 1, further comprising an electronic controller programmed to control movements of the loading system and the acquisition of the one or more digital images.

6. The machine of claim 5, wherein the microscope comprises a mobile board, the electronic controller being programmed to control movement of the mobile board, whereby a group of digital images is acquired relative to contiguous fields at a pre-determined magnification through an incremental movement of the mobile board, and to assemble the digital images of the contiguous fields.

7. The machine of claim 1, wherein the digital images are accessible from a remote location via the internet or an intranet.

8. The machine of claim 1, wherein the loading system is configured to take the test liquids or the product samples of product from the loading station, to collect one of the first slide covers from the containment station, and to collect one of the one or more slides.

9. The machine of claim 1, wherein the loading system is configured to be positioned in correspondence of the loading station to take the test liquids and the product samples and arrange the test liquids and the product samples on the one or more slides at the positioning station, and is further configured to be positioned at the containment station to collect the one or more first slide covers, arrange the one or more first slide covers on the one or more slides, and then transport the one or more slides at the analysis station for the acquisition of the digital images.

10. The machine of claim 1, wherein the containment station comprises a box-shaped device having an upperly open seat and a support plane placed inside the upperly open seat, on which the one or more first slide covers are arranged.

11. The machine of claim 1, wherein the support base is removable.

12. A method of preparing and analyzing one or more slides according to an immuno-fluorescence technique with an automated machine, comprising the steps of:
providing the automated machine comprising:
a loading station of one or more containers for holding test liquids and product samples;
a positioning station of one or more slides comprising a support base provided with a plurality of seats each configured to hold one of the one or more slides, each seat having a base and a containment frame configured to hold one slide, the positioning station being removable from the machine;
a containment station of one or more first slide covers;
an analysis station comprising a microscope for acquisition of one or more digital images at one or more magnifications;
one or more second slide covers being sized to cover the one slide arranged in one of the seats,
wherein each of the one or more second slide covers has a top surface, provided with a gripping handle, and lateral walls extending orthogonally from the top surface in a direction opposite to the gripping handle, each of the one or more second slide covers being rectangular in shape and being sized to enclose within, in a volume defined by the top surface and the lateral walls, the containment frame and the one slide disposed within the containment frame, each seat receiving silica gel and the one slide on the silica gel, so as to cause a combined effect of the one or more second slide covers with the silica gel that reduces deterioration time of substrates of the slides;
a container holding the one or more second slide covers, the container being removable; and
a loading system, mobile along perpendicular directions inside an entire area defined by the machine, the loading system removing one of the second slide covers from one of the slides positioned in one of the seats after pre-dilution of the product samples has been completed, and arranging the removed second slide covers inside the container,
wherein the loading system comprises,
a gripping device, configured to collect the one of the second slide covers and to deposit the one of the second slide covers in the container, the gripping device being further configured to carry the one of the one or more slides coupled with one of the first slide covers from the one of the seats to the microscope;
a suction device, configured to collect the one of the first slide covers from the containment station and to deposit the one of the first slide covers on the one of the one or more slides positioned in the one of the seats, and
one or more aspirating/application needles of a liquid, the gripping device, the suction device, and the one or more aspirating/application needles being jointly mobile along the perpendicular directions,
wherein the loading system is further configured to move through the loading, positioning, containment, and analysis stations to prepare the one or more slides according to a pre-defined protocol while leaving the slides on the support base, and, after said preparation of the one or more slides, move the one or more slides to the analysis station for the acquisition of the one or more digital images, and
wherein the loading system is mobile along the perpendicular directions by sliding along perpendicular sliding tracks disposed in an upper portion of the machine;
arranging, in the loading station of the automated machine, the one or more containers for holding the test liquids and the product samples;
arranging, in the positioning station of the automated machine, the one or more slides each lodged in one or more of the seats for holding the one of the one or more slides, wherein arranging the one or more slides comprises inserting the silica gel in the seat and disposing the slide on the silica gel;
covering each slide with one of the second slide covers;
arranging, in the containment station, the one or more first slide covers;
causing the loading system to move through the loading, positioning, and containment stations to prepare one or more of the slides in accordance with the pre-defined protocol and arrange the one or more slides at the analysis station comprising a-the microscope for the acquisition of the digital images at the one or more magnifications, so as to make a subsequent acquisition of one or more digital images,
wherein preparing the one or more slides comprises:
removing the respective second slide covers, once pre-dilution of the product samples has been completed, and subsequently arranging the respective second slide covers inside the container;
preparing the one or more slides in accordance with the pre-defined protocol, leaving the one or more slides in the respective seats, and
after preparing the one or more slides, applying the one or more first slide covers on the one or more slides, and moving the one or more slides to the analysis station for the subsequent acquisition of the one or more digital images.

* * * * *